United States Patent
Sakato

[11] Patent Number: 5,288,550
[45] Date of Patent: Feb. 22, 1994

[54] PRODUCTION METHOD OF NON-FITTING TYPE CAPSULE AND NON-FITTING TYPE CAPSULE PRODUCED THEREBY

[75] Inventor: Naoyuki Sakato, Tokyo, Japan

[73] Assignee: Freund Industrial Co., Ltd., Tokyo, Japan

[21] Appl. No.: 879,322

[22] Filed: May 7, 1992

[30] Foreign Application Priority Data

May 8, 1991 [JP] Japan .................................. 3-102824

[51] Int. Cl.$^5$ .............................................. B01J 13/02
[52] U.S. Cl. ........................... 428/321.5; 428/321.1; 428/402
[58] Field of Search ............... 428/402.22, 402.24, 428/914, 321.5, 321.1; 521/64; 523/201; 524/461, 819, 832; 427/213.33

[56] References Cited

U.S. PATENT DOCUMENTS

| | | | |
|---|---|---|---|
| 2,969,330 | 1/1961 | Brynko | 428/402.22 |
| 3,627,693 | 1/1971 | Scarpelli | 428/402.22 |
| 3,943,063 | 3/1976 | Morishita et al. | 428/402.22 |
| 3,965,033 | 6/1976 | Matsukawa et al. | 428/402.22 |
| 3,970,585 | 7/1976 | Matsukawa et al. | 428/402.22 |
| 4,798,691 | 1/1989 | Kasai et al. | 428/402.22 |

FOREIGN PATENT DOCUMENTS 60-9854  3/1985  Japan .

Primary Examiner—Patrick J. Ryan
Assistant Examiner—William A. Krynski
Attorney, Agent, or Firm—Kane, Dalsimer, Sullivan, Kurucz, Levy, Eisele and Richard

[57] ABSTRACT

In producing a non-fitting type capsule containing an oily substance such as vitamin E, etc. in a capsule, a hydrophilic solvent such as ethanol, etc. which can be dissolved in the oily substance is added thereinto to lower viscosity thereof.

5 Claims, 2 Drawing Sheets

PRODUCTION METHOD OF NON-FITTING TYPE CAPSULE AND NON-FITTING TYPE CAPSULE PRODUCED THEREBY

BACKGROUND OF THE INVENTION

1. Field of the Invention

The present invention relates to a production technique of a non-fitting type capsule, and more particularly to a technique for producing a non-fitting type capsule containing an oily substance.

2. Related Art Statement

Soft capsules containing a oily substance have widely been used in the fields of medicine, food, etc. These soft capsules comprise an oily substance such as medicine, i.e., oil-soluble vitamins including Vitamin A, D, E, etc., cod-liver oil, linoleic acid, etc.; healthy food: or those in which an oil-soluble medicine is dissolved in a vegetable oil, etc; being contained in an outer shell made of gelatin, etc.

In general, for preparing the above soft capsules, a rotary type automatic encapsulation machine having a structure as shown in FIG. 2 has been used.

An oily substance 11 to be filled in capsules is supplied from a tank which is not shown through a pipe into a cylinder pump 12. A gelatin sheet 13 which is to constitute an outer shell is molded into a sheet from an aqueous gelatin solution which was heated to be dissolved in a previous step which is not shown, and after transferred to a die roll 14 in a heated state, it encapsulates therein the oily substance 11 supplied by the cylinder pump 12 and is formed to be a soft capsule 15 by heat pressing. The oily substance 11 is supplied to the die roll 14 generally in a heated state so as not to lower a temperature of the heat pressing.

In the aforesaid rotary type automatic encapsulation machine, it is difficult to broaden the width of the flow passage of the oily substance in view of its structure and the oily substance is supplied from the tank to the cylinder pump by gravity-drop.

Thus, if an oily substance having high viscosity is used, a large load must be applied for suction of the cylinder pump even when the viscosity is reduced to some extent by heating, whereby working failure tends to be caused when same production speed of capsules as low viscosity oil is employed. Therefore, production speed of capsules must be lowered.

To cope with this, it may be considered to supply an oily substance by using an additional pump in combination. It, however, is difficult since suction of the oily substance by a cylinder pump is intermittent.

Also, it may be considered to lower viscosity by adding a hydrophobic solvent or other low viscosity oily substance to a high viscosity oily substance. But, as a hydrophobic solvent, there is no suitable material which can be utilized together with medicine, food, etc. On the other hand, as shown in Table 1 below, an oily substance has generally much higher viscosity than a hydrophobic solvent, so that a viscosity lowering effect is small even when another oily substance with lower viscosity is added. As can be seen from these facts, it is the present situation that soft capsules containing a high viscosity oily substance cannot be produced with high efficiency.

TABLE 1

| Viscosities of various kinds of oily substances | | |
|---|---|---|
| Oily | Viscosity (cps) | |
| substance | 25° C. | 37.7° C. |
| Vitamin E | 320 | |
| Castor oil | 651 | 263–290 |
| Olive oil | 75 | 43 |
| Rapeseed oil | 82 | 51 |
| Soybean oil | | 28.49 |
| Liver oil (Codfish) | | 32.79 |

(Vitamin E is a measured value by the inventor, others are values shown in "Yushi Kagaku Binran" ("Oil and Fats Chemistry Handbook", in Japanese)

SUMMARY OF THE INVENTION

The present invention has been accomplished in view of the above problems, and an object thereof is to provide a technique for improving production efficiency of a non-fitting type capsule containing a high viscosity oily substance therein.

A production method of a non-fitting type capsule according to the present invention comprises adding into an oily substance a hydrophilic solvent which dissolves therein and enclosing them in a capsule.

Until now, there has not been reported to add a hydrophilic solvent into an oily substance contained in a soft capsule since problems of incompatibility between the oily substance and the hydrophilic solvent, stability, malignant effects on a capsule skin, etc. have been considered. The present inventor, however, has dared to attempt it, and has found that viscosity lowering effect on an oily substance is remarkable and unexpectedly there is no substantial problem in compatibility, stability, effects on a capsule skin.

FIG. 1, for example, shows the viscosity lowering effect of ethanol which is added as a hydrophilic solvent to vitamin E as an oily substance. As clearly seen from FIG. 1, falling of viscosity by adding ethanol to vitamin E is non-linear, being far more abrupt than expected.

As the results, production efficiency of soft capsules containing vitamin E can be markedly improved. In this case, the improving effect as expected from the above discovery can be obtained by adding only 1 to 10% by weight, preferably about 2 to 5% by weight of ethanol based on the total weight of Vitamin E and ethanol.

A kind of an oily substance used in the present invention is not limited, and there may be included, for example, vegetable oils and fats; fish oils and fats and purified products thereof; animal oils and fats and purified products thereof; an oil-soluble vitamins such as vitamins A, D and E; unsaturated higher fatty acids such as linoleic acid; glycerol esters of higher fatty acids; glycerol esters of middle fatty acids; polyglycerol esters; paraffins; terpenes; and mixtures of these.

The hydrophilic solvent to be used in the present invention may vary depending on the kind of an oily substance, but there may be generally included (1) lower fatty alcohols such as methanol and ethanol; (2) lower fatty acids such as acetic acid; (3) lower alcohol esters of lower fatty acids such as methyl acetate and ethyl acetate; and (4) lower fatty ketones such as acetone. For use with medicine or food, ethanol, acetic acid, ethyl acetate are particularly preferred. For reference purpose, viscosities of ethanol, acetic acid and ethyl acetate are shown in the following Table 2.

TABLE 2

| Hydrophilic solvent | Viscosities of hydrophilic solvents allowable as food additives | | |
|---|---|---|---|
| | Viscosity (cps) | | |
| | 20° C. | 30° C. | 40° C. |
| Ethanol | 1.19 | 1.00 | 0.825 |
| Acetic acid | 1.22 | 1.04 | 0.90 |
| Ethyl acetate | 0.449 | 0.400 | 0.360 |

(According to "Yushi Kagaku Binran")

Following Tables 3, 4 and 5 show the viscosity lowering effects of ethanol and acetone which are added to castor oil and of ethyl acetate which is added to liquid paraffin.

TABLE 3

Viscosities of Castor oil/Ethanol mixtures at 23° C.

| % by weight of ethanol | Viscosity (cps) | Measuring conditions |
|---|---|---|
| 0% | 770 | Rotor No. 2, 30 rpm |
| 2% | 651 | " |
| 5% | 456 | " |
| 10% | 287 | " |

TABLE 4

Viscosities of Castor oil/Acetone mixtures at 23° C.

| % by weight of acetone | Viscosity (cps) | Measuring conditions |
|---|---|---|
| 0% | 770 | Rotor No. 2, 30 rpm |
| 2% | 525 | " |
| 5% | 328 | " |
| 10% | 171 | Rotor No. 2, 60 rpm |

TABLE 5

Viscosities of Liquid paraffin/Ethyl acetate mixtures at 23° C.

| % by weight of ethyl acetate | Viscosity (cps) | Measuring conditions |
|---|---|---|
| 0% | 150 | Rotor No. 1, 30 rpm |
| 2% | 126.2 | " |
| 5% | 93.0 | " |
| 10% | 59.3 | Rotor No. 1, 60 rpm |

Differently from other percent values in the present invention, the percent values shown in these Tables 3, 4 and 5 are based on castor oil and liquid paraffin respectively not on total mixtures.

Also, to these oily substances and/or hydrophilic solvents, other medicinal materials, nutrients, seasoning agents, coloring agents, perfumes, surfactants, etc. may be optionally added. These additives may be added in the state that they are solved, dispersed or emulsified in the oily substance and/or the hydrophilic solvent.

As medicinal materials, there may be listed, for example purpose, drugs for central nervous system and for peripheral nervous system, drugs for allergic diseases, drugs for circulatory organs, drugs for inspiratory organs, drugs for digestive organs, hormon drugs, vitamin preparations, nourishing and tonic medicines, other metabolizable medicines, medicines for tumor, antibiotic preparations, chemotherapeutic agents, and biological agents such as vaccines.

Medicinal materials may be added by solving in a hydrophilic solvent even if they can not be solved in the oily substances. For example, as medicinal materials soluble in ethanol, there may be listed isosorbide dinitrate, propranolol hydrochloride, diclofenac sodium, flufenamic acid, ibuprofen, phenylbutazone, flurbiprofen, ketoprofen, cefalexin, griseofulvin, chloramphenicol, and erythromycin, soysterol, tocopherol nicotinate, gefarnate, and dextromethorphan hydrobromide.

On the other hand, furosemide, prozosin hydrochloride, dipyridamole, cefaclor, tetracycline, ampicillin, piroxicam, fenbufen, indomethacin, nifedipine, diltiazem hydrochloride, insulin, ubidecarenone, bromhexine, hydrochloride, lysozyme chloride, and bromelain can be added by dispersing in ethanol.

These medicinal materials are listed for example purpose only, and the present invention should not be limited to these medicinal materials.

As nutrients, there may be listed, for example, vitamins, amino acids and minerals.

As seasoning agents, there may be listed, for example, sweetenings, sour agents, meat extracts and condiments.

As coloring agents, are listed synthesized coloring agents and natural coloring agents.

As perfumes, there may be listed synthesized perfumes and natural perfumes such as mint, cinnamon, cassia, rose, clove and anise.

As surfactants, there may be listed nonionic surfactant such as fatty acid ester of sorbitan, fatty acid ester of saccharose, polyoxiethylene and fatty acid ester of polyglycerol; anionic surfactant such as fatty acid soaps; and cationic surfactant such as quaternary ammonium salts.

These lists of additives also are only for example purpose, and the present invention should not be limited to these listed substances.

Also, a substance for an outer shell of the capsule is not limited and may be optionally a gelatin, an agar, an alginate, a substance which dissolves when it reaches human intestine, etc.

The production method of the present invention can be applied not only to the usual preparation of a soft capsule as mentioned above, but also to a preparation of a seamless capsule in which liquids flow of an oily substance as a core liquid and an outer liquid which forms an outer shell of the capsule are dropped from a double nozzle to form double-layered liquid drops and then the above outer liquid is hardened by a chemical reaction or cooling with a hardening liquid.

In this case of the seamless capsule, also by lowering viscosity of an oily substance by adding a hydrophilic solvent, passing of the oily substance through the nozzle becomes easy so that production efficiency of a seamless capsule can be improved.

As in the case of soft capsules, production efficiency of seamless capsules containing a oily substance can be markedly improved by adding only 1 to 20% by weight of a hydrophillic solvent based on the total weight of the oily substance and the hydrophillic solvent.

In the present invention, "a non-fitting type capsule" means the above soft capsule and the seamless capsule inclusively.

According to the production method of the present invention, the following effects are found by the present inventor, in addition to the above effects.

(1) Medical components, etc. which do not dissolve in an oily substance can be dissolved in a hydrophilic solvent and enclosed in a capsule. The medicinal material, etc. dissolved in the hydrophilic solvent may sometimes precipitate in the oily substance. Even in that case, however, they are dispersed or emulsified in the oily substance in many cases, so that there is no serious problem.

(2) When the present invention is applied to the production method of the seamless capsule, because of decreased viscosity, a capsule easily deforms at unhardened state as a liquid drop blown from a nozzle falls within a hardening liquid, whereby a highly spherical capsule is obtained.

(3) In the case of the production method of the seamless capsule, in addition to the above effect (2), a density of an oily substance can be made substantially equal to that of the outer shell by suitably selecting a kind of a hydrophilic solvent, whereby the liquid contained in the capsule can be prevented from being eccentric.

DETAILED DESCRIPTION OF THE PREFERRED EMBODIMENT

EXAMPLE 1

Figure 1:
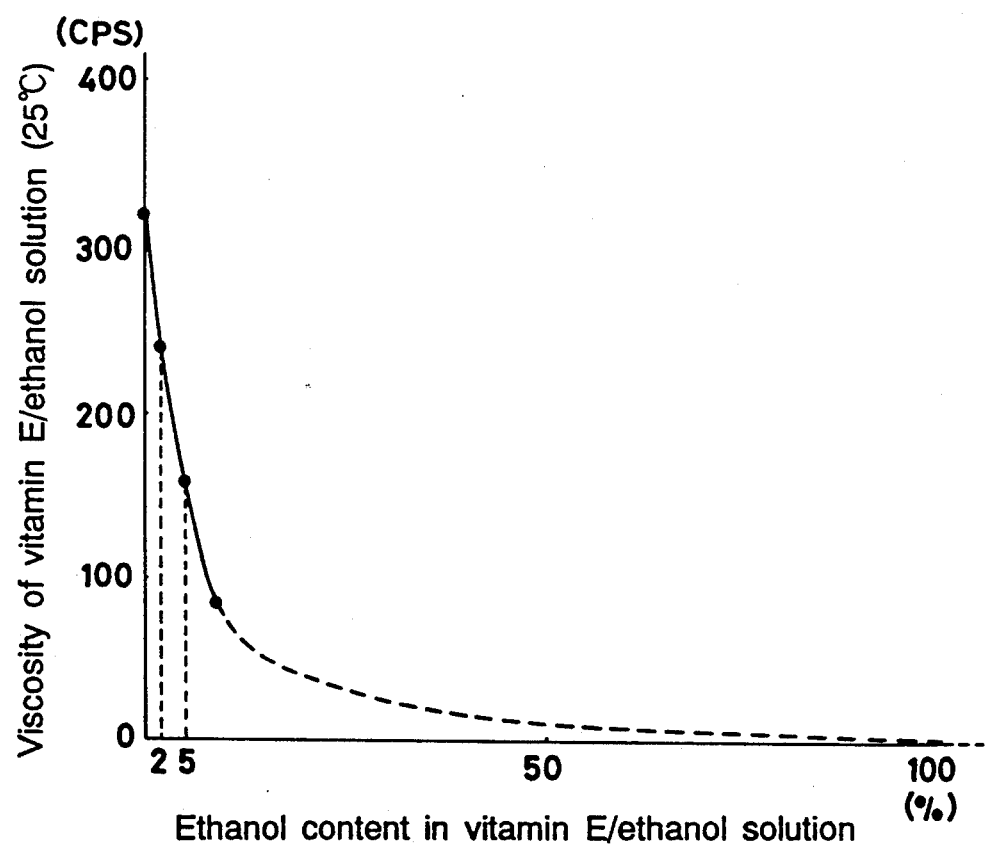
FIG. 1 is a graph showing a relationship between an addition ratio of ethanol to vitamin E and viscosity of the mixture.
Figure 2:
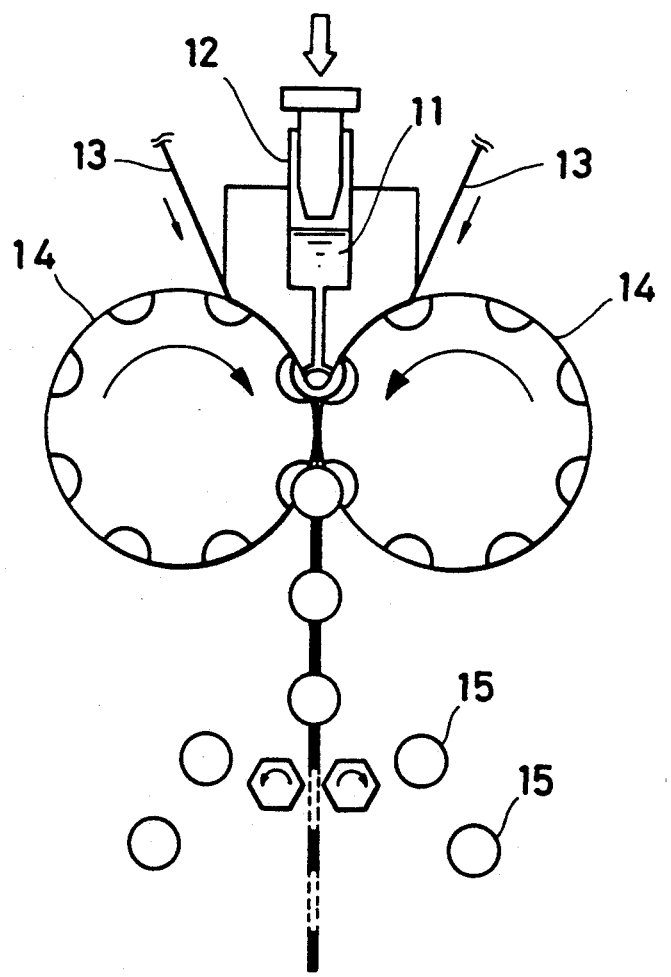
FIG. 2 is a schematic view showing main portion of a rotary type automatic encapsulation machine to be used for preparation of a soft capsule.

By using an encapsulation machine (a "RG-082" model) manufactured by Nippon Yakugyo Kikai K.K., vitamin E was tried to be filled into an outer shell made of gelatin at a conventional operating condition, i.e. production speed of 350 capsules/minute, but it could not be filled since flowability of vitamin E was poor. Then, a filling rate was decreased but a capsule could not be formed since a temperature of the gelatin sheet was lowered.

On the other hand, vitamin E to which 2.5% by weight of ethanol was added could be filled smoothly in the same conditions as mentioned above.

EXAMPLE 2

In the same conditions as mentioned in Example 1, it was tried to fill castor oil into an outer shell made of gelatin, but it was not possible because flowability of castor oil was poor. On the other hand, a castor oil to which 10% by weight of ethanol was added could be filled smoothly.

EXAMPLE 3

In the same conditions as in Example 1, acetone 10% by weight was added to castor oil, and the castor oil could be filled smoothly.

EXAMPLE 4

A multi-layer liquid drop preparation apparatus disclosed in Japanese Patent Publication No. 60-9854 was used and also a concentric double nozzle (inner nozzle diameter=0.2 mm$\phi$, outer nozzle diameter=0.5 mm$\phi$) disclosed in Example of said publication was used as a nozzle. Using a 4% agar aqueous solution as an outer shell liquid, it was tried to fill rapeseed oil as a core solution thereinto, but jet-like injection could not be obtained since flow rate of rapeseed oil was insufficient. Thus, desired seamless capsule could not be obtained.

On the other hand, when 10% by weight of ethyl acetate was added to rapeseed oil, flow rate thereof was improved and good jet-like injection could be obtained. Thus, rapeseed oil could be filled into agar solution to obtain a desired seamless capsule.

EXAMPLE 5

In the same conditions as in Example 4, it was tried to fill a liquid paraffin as a core solution into an outer shell of a 4% agar aqueous solution, but jet-like injection could not be obtained since flow rate of liquid paraffin was insufficient.

On the other hand, when 15% by weight of ethyl acetate was added to a liquid paraffin, flow rate thereof was improved and good jet-like injection could be obtained. Thus, rapeseed oil could be filled into agar solution to obtain a desired seamless capsule.

Thus, when preparing a non-fitting type capsule containing an oily substance, by adding a hydrophilic solvent which can be dissolved in the oily substance thereinto, production efficiency of the non-fitting capsule can be improved.

What is claimed is:

1. A non-fitting type capsule, comprising an oily substance and a hydrophilic solvent which dissolves in the oily substance, as contents of the capsule.

2. The non-fitting type capsule according to claim 1 wherein:
   the hydrophilic solvent is selected from the group consisting of methanol, ethanol, acetic acid, methyl acetate, ethyl acetate, and acetone.

3. The non-fitting type capsule according to claim 1 wherein:
   the oily substance is selected from the group consisting of vegetable oils, vegetable fats, fish oils, fish fats, animal oils, animal fats, oil-soluble vitamins, unsaturated higher fatty acids, glycerol esters of fatty acids, polyglycerol esters, paraffins, terpenes, and mixtures thereof.

4. The capsule according to claim 3 wherein the glycerol esters of fatty acids is selected from the group consisting of glycerol esters of middle fatty acids and glycerol esters of higher fatty acids.

5. The non-fitting type capsule according to claim 1, wherein:
   the capsule further comprises a constituent selected from the group consisting of medicinal materials, nutrients, seasoning agents, coloring agents, perfumes and surfactants.

* * * * *